(12) United States Patent
Fortunato et al.

(10) Patent No.: US 6,403,078 B2
(45) Date of Patent: *Jun. 11, 2002

(54) METHOD AND COMPOSITIONS FOR TREATING PRETERM LABOR AND PREMATURE RUPTURE OF FETAL MEMBRANES

(76) Inventors: Stephen Joseph Fortunato, 9405 Atherton Ct., Brentwood, TN (US) 37027; Ramkumar Menon, 610 Erin La., Nashville, TN (US) 37221

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/234,326

(22) Filed: Jan. 20, 1999

Related U.S. Application Data

(60) Provisional application No. 60/071,833, filed on Jan. 20, 1998.

(51) Int. Cl.[7] .......................... A61K 45/00; A61K 38/00; A61K 38/16; A01N 25/00
(52) U.S. Cl. .............................. 424/85.2; 514/2; 514/8; 514/12; 514/885
(58) Field of Search .............................. 424/85.2, 85.1; 514/2, 8, 12, 885

(56) References Cited

U.S. PATENT DOCUMENTS

| | | | | |
|---|---|---|---|---|
| 5,837,293 A | * | 11/1998 | Malefyt et al. | ............. 424/85.2 |
| 5,873,293 A | | 11/1998 | Malefyt et al. | ............. 424/852 |

OTHER PUBLICATIONS

Fortunato et al. American Journal of Obstetrics and Gynecology. vol. 175, No. 4 part 1, pp. 1057–1065, Oct. 1996.*

Gravett et al., An Experimental model for intraamniotic infection and preterm labor in rhesus monkeys, Am. J. Obstet. Glyncol.. 1994; 171:1660–1667.*

Spencer et al., Interleukin–10 (IL–10) inhibits prostaglandin E–2 (PGE–2) and interleukin–6 (IL–6) production in human decidual cells: A potential role in preterm labor(1995). J. of Investigative Medicine, vol. 43, Suppl. 1, p 186A (abstract only).*

Casey ML and McDonald PC, "Biomolecular processes in the initiation of parturition: decidual activation." *Clin Obstet Gynecol.*, Sep. 1988; 31(3):533–52.

Cox SM et al., "Accumulation of interleukin–1beta and interleukin–6 in amniotic fluid: a sequela of labour at term and preterm." *Hum Reprod Update*, Sep.–Oct. 1997; (5):517–27.

Dudley DJ et al., "Amniotic fluid interleukin–10 (IL–10) concentrations during pregnancy and with labor." *J Reprod Immunol*, Jun. 1997; 33(2):147–56.

Dudley DJ et al., Regulation of decidual cell and chorion cell production of interleukin–10 by purified bacterial products. *Am J Reprod Immunol*, Oct. 1997; 38(4):246–51.

Dudley DJ, "Pre–term labor: an intra–uterine inflammatory response syndrome?" *J Reprod Immunol*, Nov. 30, 1997; 36(1–2):93–109.

Edwin SS et al., "Action of immunoregulatory agents on 5–HETE production by cultured human amnion cells." *J Reprod Immunol*, Nov. 30, 1997; 36(1–2):111–21.

Fortunato SJ et al., "Inflammatory cytokine (interleukins 1, 6, and 8 and tumor necrosis factor–α) release from cultured human fetal membranes in response to endotoxic lipopolysaccharide mirrors amniotic fluid concentrations." *Am J Obstet Gynecol*, Jun. 1996; 174(6): 1855–1862.

Fortunato SJ et al., "Interleukin–10 and transforming growth factor–β inhibit amniochorion tunor necrosis factor–α production by contrasting mechanisms of action: Therapeutic implications in prematurity." *Am J Obstet Gynecol*, Oct. 1997; 177(4):803–809.

Fortunato SJ et al., "Interleukin–10 inhibition of interleukin–6 in human fetal membranes: transcriptional regulation." *Am J Obstet Gynecol*, 1996. 175:1057–65.

Gomez et al., "The role of infection in preterm labor and delivery." In:*Preterm Labor*, Eds., Elder et al., 1997, Churchill Livingstone, pp. 85–125.

Gomez R et al., "Premature labor and intra–amniotic infection. Clinical aspects and role of the cytokines in diagnosis and pathophysiology." *Clin Perinatol.*, Jun. 1995; 22(2):281–342.

Gomez R et al.,"Pathogenesis of preterm labor and preterm premature rupture of membranes associated with intraamniotic infection." *Infect Dis Clin North Am.*, Mar. 1997; 11(1):135–76.

(List continued on next page.)

*Primary Examiner*—Gary L. Kunz
*Assistant Examiner*—Jegatheesan Seharaseyon
(74) *Attorney, Agent, or Firm*—Law Office of Kenneth K. Sharples

(57) ABSTRACT

Methods and compositions for the prevention and treatment of preterm labor and premature rupture of fetal membranes are provided. The methods of the invention inhibit the upregulated production of certain pro-inflammatory cytokines in amniochorionic membranes, including IL-6, IL-8 and TNF-α, and inhibit preterm labor and the premature rupture of fetal membranes. The practice of the method of the invention using the cytokine IL-10 is specifically described. IL-10 demonstrates the capacity to inhibit pro-inflammatory cytokine production in amniochorionic membranes in vitro as well as the capacity to inhibit uterine contractility and preterm labor in rhesus monkeys in vivo. The methods of the invention may be particularly useful in preventing infection-induced preterm labor and premature rupture of fetal membranes as well as preterm labors with a non-infectious etiology.

7 Claims, 9 Drawing Sheets

OTHER PUBLICATIONS

Figure 1:
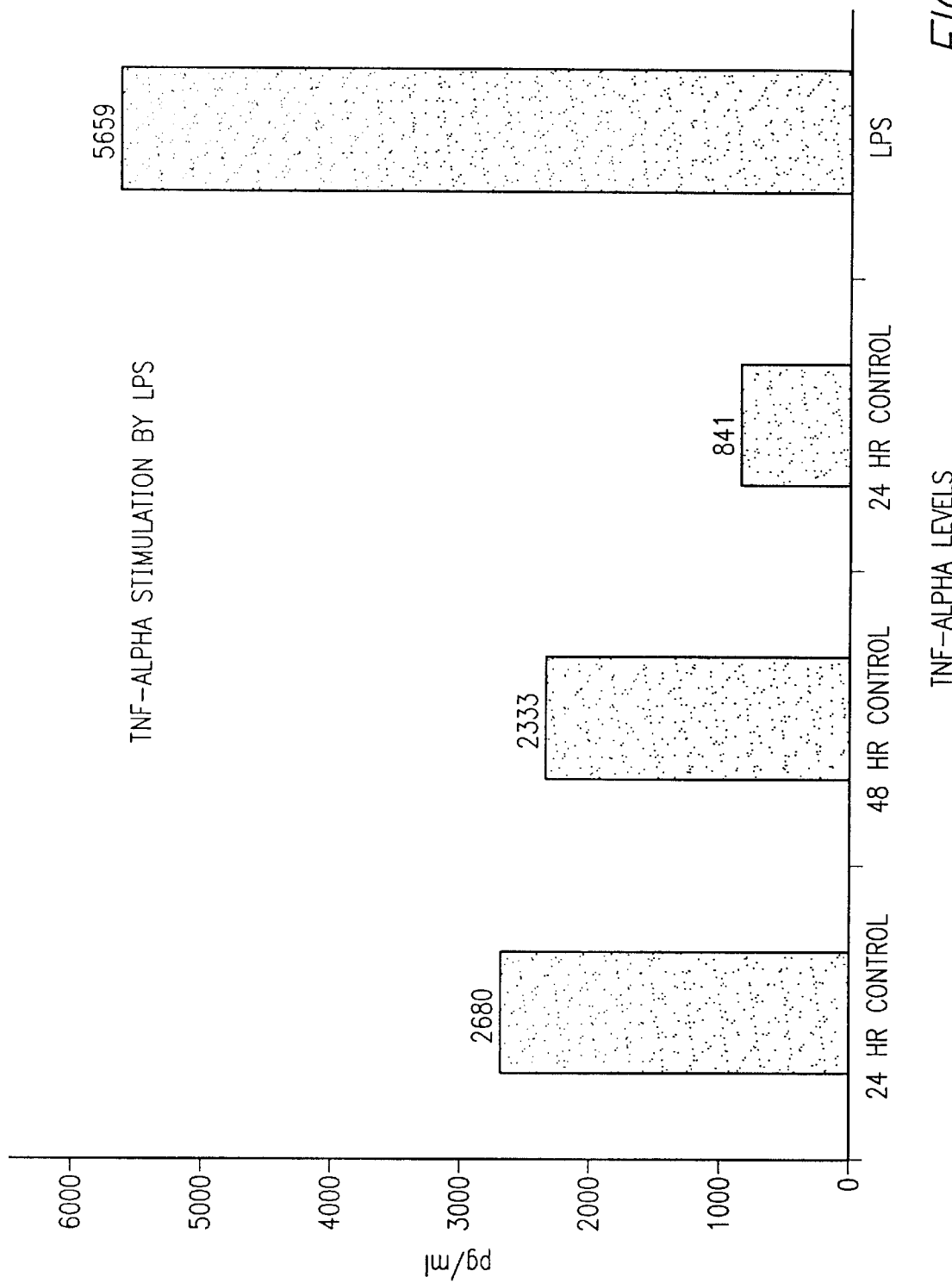

Gravett MG et al, "Interleukin–10 inhibits interleukin–1β indiced preterm labor in rhesus monkeys." Abstract as submitted for Annual Scientific Meeting of the Infectious Disease Society for Obstetrics and Gynecology, Aug. 5–8, 1998. The details and complete results of the described study are incorporated in Example 3 of the subject application.

Greig PC et al., "Amniotic fluid interleukin–10 concentrations increase through pregnancy and are elevated in patients with preterm labor associated with intrauterine infection." *Am J Obstet Gynecol,* Oct. 1995; 173(4):1223–7.

Hertelendy F et al., "Cytokine–initiated signal transduction in human myometrial cells." *Am J Reprod Immunol.,* Sep.–Oct. 1993; 30(2–3):49–57.

Keelan JA et al., "Interleukin–10 has opposing actions on cytokine production in amnion and choriodecidual explants." J Soc Gynecol Invest, 4(1)(suppl.) Jan.–Feb. 1997; 167A, Abstract 351.

Keelan JA et al., "Interleukin–10 stimulates production of hydroxy–eicosatetraenoic acids, while inhibiting cytokine production, in choriodecidual explants." J Soc Gynecol Invest, 4(1)(suppl.) Jan.–Feb. 1997; 221A, Abstract 563.

Keelan JA et al., "The molecular mechanisms of term and preterm labor: recent progress and clinical implications." *Clin Obstet Gynecol.,* Sep. 1997; 40(3): 460–78.

MacDonald PC et al., "Parturition: Biomolecular and physiologic processes." In: Williams Obstetrics, Eds., Cunningham et al., 1993, Appleton & Lange, pp. 297–361. See pp 350–356.

MacDonald PC, Casey ML, "The accumulation of prostaglandins (PG) in amniotic fluid is an aftereffect of labor and not indicative of a role for PGE2 or PGF2 alpha in the initiation of human parturition." *J Clin Endocrinol Metab.,* May 1993; 76(5): 1332–9.

Menon R et al., "Expression of inflammatory cytokines (interleukin–1β and interleukin–06) in amniochorionic membranes." *Am J Obset Gynecol,* Feb. 1995; 172: 493–500.

Mitchell MD et al., "Cytokine networking in the placenta." *Placenta,* 1993; 14: 249–275.

Oshiro BT et al., "Endotoxin, interleukin–1 beta, interleukin–6, or tumor necrosis factor–alpha do not acutely stimulate isolated murine myometrial contractile activity." *Am J Obstet Gynecol.,* Dec. 1993; 169(6): 1424–7.

Trautman MS et al., "Expression of interleukin–10 in human gestational tissues." *J Soc Gynecol Investig,* Sep.–Oct. 1997; 4(5):247–53.

Gravett MG et al., "An experimental model for intraamniotic infection and preterm labor in rhesus monkeys." *Am J Obstet Gynecol,* 1994; 171: 1660–1667.

Fortunato et al., "IL–10 inhibits IL–8 production by human amniochorionic membrane." Transcription of poster (text only) presented at Second Annual Cytokine Antagonists Conference, Cambridge Health Tech Institute, Boston, Nov. 1995. The Abstract of the poster is believed to be identical to the Abstract as published in the Proceedings of the conference; however, no copy of the Abstract as published is available.

Fortunato SJ et al., "Interleukin–10 and transforming growth factor–β inhibit amniochorion tumor necrosis factor–α production by contrasting mechanisms of action: Therapeutic implications in prematurity." *Abstract presented at the 1997 Annual Meeting of the Society of Perinatal Obstetricians,* Jan. 20–25, 1997. *Am J Obstet Gynecol,* Jan. 1997; 176:S41 [abstract No. 105].

Fortunato SJ et al., "The effect of transforming growth factor and interleukin–10 on interleukin–8 release by human amniochorion may regulate histologic chorioamnionitis." *Am J Obstet Gynecol,* Sep. 1998; 179(3): 794–799.

Fortunato SJ et al., "The effect of transforming growth factor and interleukin–10 on interleukin–8 release by human amniochorion may regulate histologic chorioamnionitis." *J Soc Gynecological Invest, Abstracts of the 44${}^{th}$ Annual Meeting,* Mar. 19–22, 1997; 4(1)(suppl):Jan./Feb. 1997 [abstract No. 315].

Fortunato SJ et al., "Amniochorion: A source of Interleukin–8." *Am J Reproductive Immunol,* 1995; 34:156–162.

Fortunato et al., "Expression of interleukin–8 and interleukin–12 by human fetal membranes." *Am J Obstet Gynecol,* 1995; 172:281 [abstract 71].

Fortunato SJ et al., "Expression of inflammatory cytokines (interleukin–1β and interleukin–6) in amniochorionic membranes." *Am J Obstet Gynecol,* 1995; 172: 493–500.

Fortunato SJ et al., "Organ Culture of Amniochorionic Membrane In Vitro." *Am J Reproductive Immunol,* 1994; 32:184–187.

Fortunato SJ et al., "Expression of TNF–α and TNFR p55 in Cultured Amniochorion." *Am J Reproductive Immunol,* 1994; 32:188–193.

\* cited by examiner

LPS STIMULATION OF TNF

A=LPS; B=LPS STIMULATION AFTER A 6HR IL-10; C=
IL-10 TREATMENT AFTER A 6HR LPS STIMULATION; D=
CONTROL

METHOD AND COMPOSITIONS FOR TREATING PRETERM LABOR AND PREMATURE RUPTURE OF FETAL MEMBRANES

This application claims priority under 35 USC 120 to U.S. provisional patent application Ser. No. 60/071,833, filed Jan. 20, 1998, the contents of which are hereby incorporated by reference herein in its entirety.

Throughout this application, various publications are referenced within parentheses. The disclosures of these publications are hereby incorporated by reference herein in their entireties.

BACKGROUND OF THE INVENTION

Prematurity is the single largest contributor to neonatal mortality (Van den Berg and Oeshsli: Prematurity. In: Bracken, M B (Ed): Perinatal Epidemiology. Oxford Univ Press, London, 1984, p. 69). It has been reported that the premature rupture of the fetal membranes (PROM) is associated with one third of all preterm deliveries and is the third leading cause of perinatal death (Gibbs et al., 1982, Obstet Gynecol 60: 671–79). Microbial invasion of the amniotic cavity followed by intra uterine inflammation has been documented as the major factor associated with the outcome of preterm labor (Gomez et al., 1995, Clin Perinatal 22: 281–342) and is associated with greater than half of the incidences of preterm labor and premature rupture of the fetal membrane. The main morbidities associated with preterm labor include fetal or infant death, respiratory distress, severe intraventricular hemorrhage, necrotizing enterocolitis, and sepsis.

The immune response to microbial invasion of the amniotic cavity is characterized by the infiltration of polymorphonuclear leukocytes (PMNs) into the placental membranes. Acute inflammation of the amniochorion as determined by the presence of PMNs in the fetal membranes (histologic chorioamnionitis) is considered to be a marker of intraamniotic infection. Clinically silent histologic chorioamnionitis is seen in up to 80% of the cases of preterm labor unresponsive to tocolysis, many of which may present no other evidence of disease (Pankuch et al., 1984, Obstet Gynecol 64: 802–806; Cherouny et al., 1993, Am J Obstet Gynecol 253: 9–14).

It is widely accepted that the biomolecular events and pathophysiologic derangements associated with infections are mediated by endogenous products of the host immune response, such as interleukin-1 (IL-1), interleukin-6 (IL-6), interleukin-8 (IL-8) and tumor ecrosis factor-alpha (TNF-α) (Gomez et al, 1995, supra). Maternal tissues (decidua and residual macrophages) and fetal tissues (amniochorion) are rich sources of these proinflammatory cytokines. IL-1, IL-6, and TNF-α are all capable of activating pathways which lead to increased production of uterotonins such as prostaglandins, endothelins, PAF, etc. IL-8 can attract and activate polymorphonuclear leukocytes leading to an increase in the overall process of inflammation in uterine tissues (Gomez et al., 1995, Clin Perinatol 22: 281–342). TNF-α can induce prostaglandin production from placental tissue and can induce preterm labor in animals (Casey et al., 1989, J Clin Invest 83: 430–436; Romero et al., 1992, Am J Obstet Gynecol 166: 1576–87). The levels of these proinflammatory cytokines released from human fetal membranes in response to bacterial lipopolysaccharide mimics the levels of these molecules in the amniotic fluid during MIAC (Fortunato et al., 1996, Am J Obstet Gynecol 174: 1855–62).

Although the role of inflammatory cytokines and their possible role in MIAC has been studied extensively, the potential role of the immunomodulatory cytokines in this process has not been established. IL-10 is an immunoinhibitory cytokine produced by T lymphocytes, monocytes and macrophages. Along with proinflammatory cytokines, IL-10 levels have been shown to be increased in the amniotic fluid of women with infection associated preterm labor (Grieg et al., 1995, Am J Obstet Gynecol 173: 1223–27).

There is currently no effective means of reliably preventing preterm labor associated with intraamniotic infection as well as preterm labors associated with unknown etiologies. Antibiotic therapy has been shown to prolong the pregnancies in PROM but not in preterm labor, however, the effect on infant morbidity has been inconsistent and the use antibiotics have achieved only modest success as a treatment modality (see, for example, Mercer et al., 1997, J Am Med Assoc 278: 989–995). In addition, calcium channel blockers, steroids, prostaglandin inhibitors, and β-sympathomimetic drugs are also commonly used to treat patients with infection, preterm labor and premature rupture of the membranes. Although these treatments are capable of inhibiting myometrial contractility, they have proven less than desirable for effectively treating clinical preterm labor and produce toxic side-effects which limit their utility. Accordingly, there is a great need for improved treatment modalities capable of preventing premature rupture of the membranes and preterm labor associated with intraamniotic infection in order to reduce the unacceptably high level of mortality, morbidity and cost resulting from these conditions.

SUMMARY OF THE INVENTION

The present invention provides methods and compositions for the prevention and treatment of preterm labor and premature rupture of fetal membranes. In one aspect, the method of the invention comprises inhibiting the upregulated production of certain pro-inflammatory cytokines in amniochorionic membranes, including IL-6, IL-8 and TNF-α, molecules which applicants regards as key proinflammatory cytokines involved in a cascade of cytokine-influenced and cytokine-promoted inflammation and matrix degeneration that ultimately leads to premature rupture of the membranes and preterm labor. In a particular embodiment described herein, IL-10 is used to achieve the inhibition of cytokine production. In a related embodiment, the method of the invention comprises Linhibiting uterine contractility and preterm labor by contacting the amniochorionic membrane with IL-10. The methods of the invention may be particularly useful in preventing infectioniduced preterm labor and premature rupture of fetal membranes as well as preterm labors with a non-infectious etiology.

The invention is based, in part, on discovering that the cytokine interleukin-10 (IL-10) is capable of transcriptionally inhibiting bacterial lipopolysaccharide-induced upregulated expression of IL-6, IL-8 and TNF-α in amniochorionic membranes in a dose-dependent manner and that this effect is complete at threshold concentrations. In addition, as described in the Examples which follow, IL-10 treatment of pregnant rhesus macaques experimentally induced to enter preterm labor with IL-β results in an almost complete inhibition of uterine contractility and preterm labor. Treatment with IL-10 in vivo demonstrates safety, efficacy and long half-life. Preferred embodiments of the invention utilize IL-10 or IL-10 activating substances capable of inhibiting infection-induced uterine contractility and preterm labor.

BRIEF DESCRIPTIONS OF THE FIGURES

FIG. 1. ELISA performed on cultured media samples shows increased release of TNF-α peptide from LPS-stimulated samples.

Figure 2:
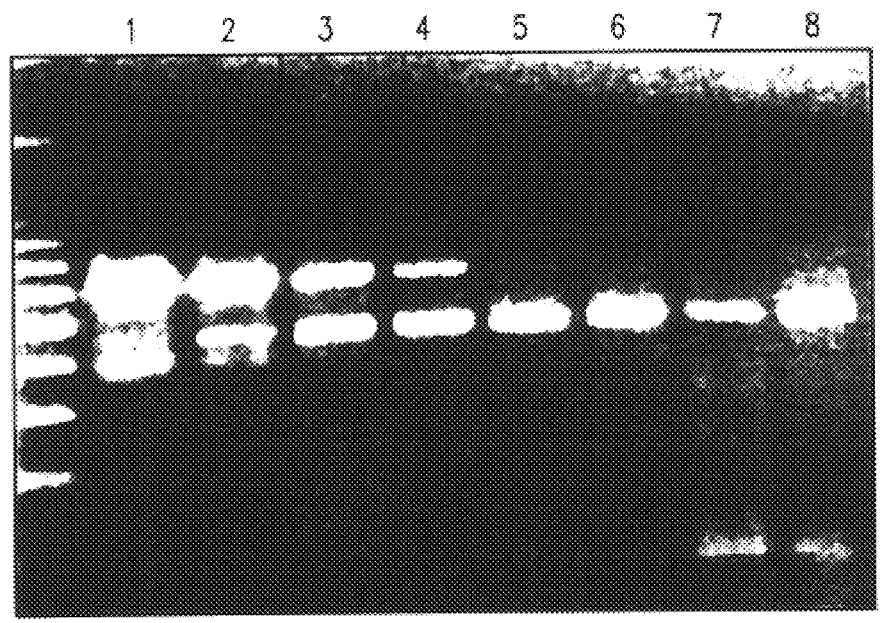

FIG. 2. TNF-α mRNA expression in LPS-stimulated amniochorionic membrane as determined by quantitative competitive polymerase chain reaction, demonstrating the presence of ~60,000 molecules of TNF-α mRNA.

Figure 3A:
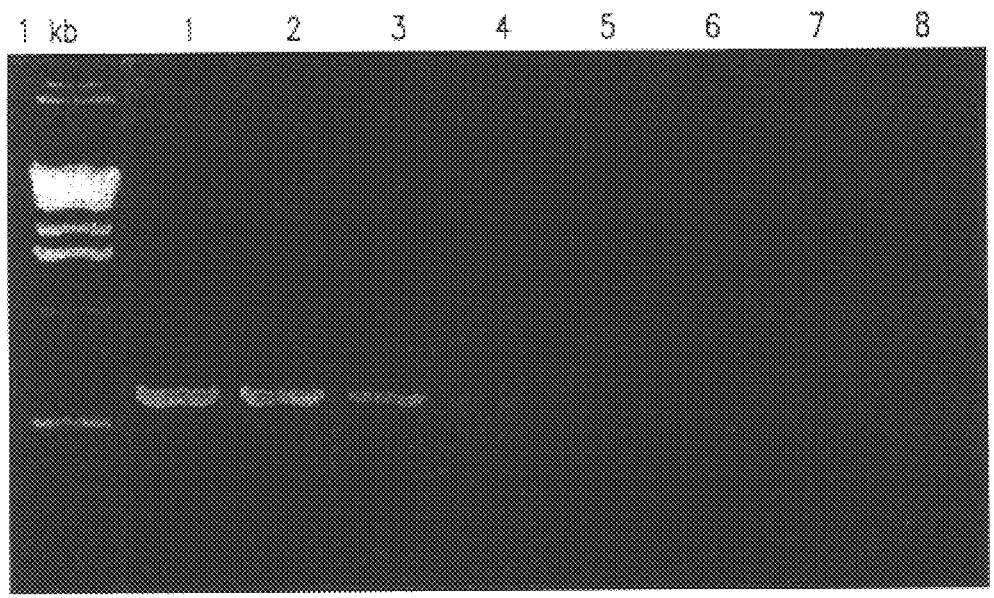
Figure 3B:
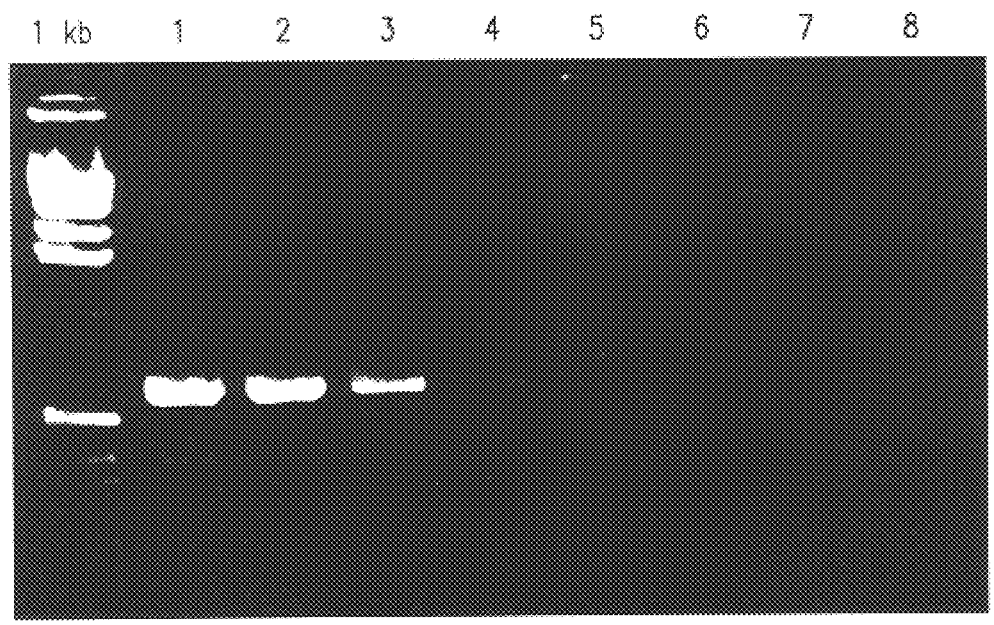

FIGS. 3A–3B. Dose-dependent inhibition of TNF-α mRNA expression in lipopolysaccharide (LPS)-stimulated amniochorionic membranes treated with IL-10 as determined by quantitative competitive polymerase chain reaction: (A) amniochorionic membranes stimulated with 50 ng/ml LPS plus 50 ng/ml IL-10 exhibit a ten-fold inhibition of TNF-α mRNA expression (~6,000 molecules TNF-α mRNA per microliter DNA) compared to membranes treated with LPS alone; (B) amniochorionic membranes stimulated with 50 ng/ml LPS plus 100 ng/ml IL-10 exhibit a one hundred-fold inhibition of TNF-α mRNA expression (~600 molecules TNF-α mRNA per microliter DNA), compared to membranes treated with LPS alone.

Figure 4:
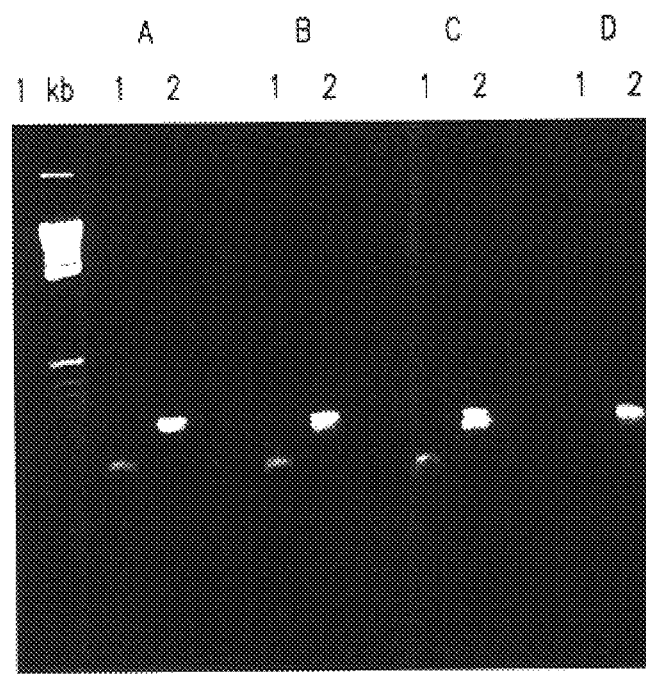

FIG. 4. TNF-α mRNA expression in pre and post infection samples after IL-10 treatment as determined by RT-PCR.

Figure 5:
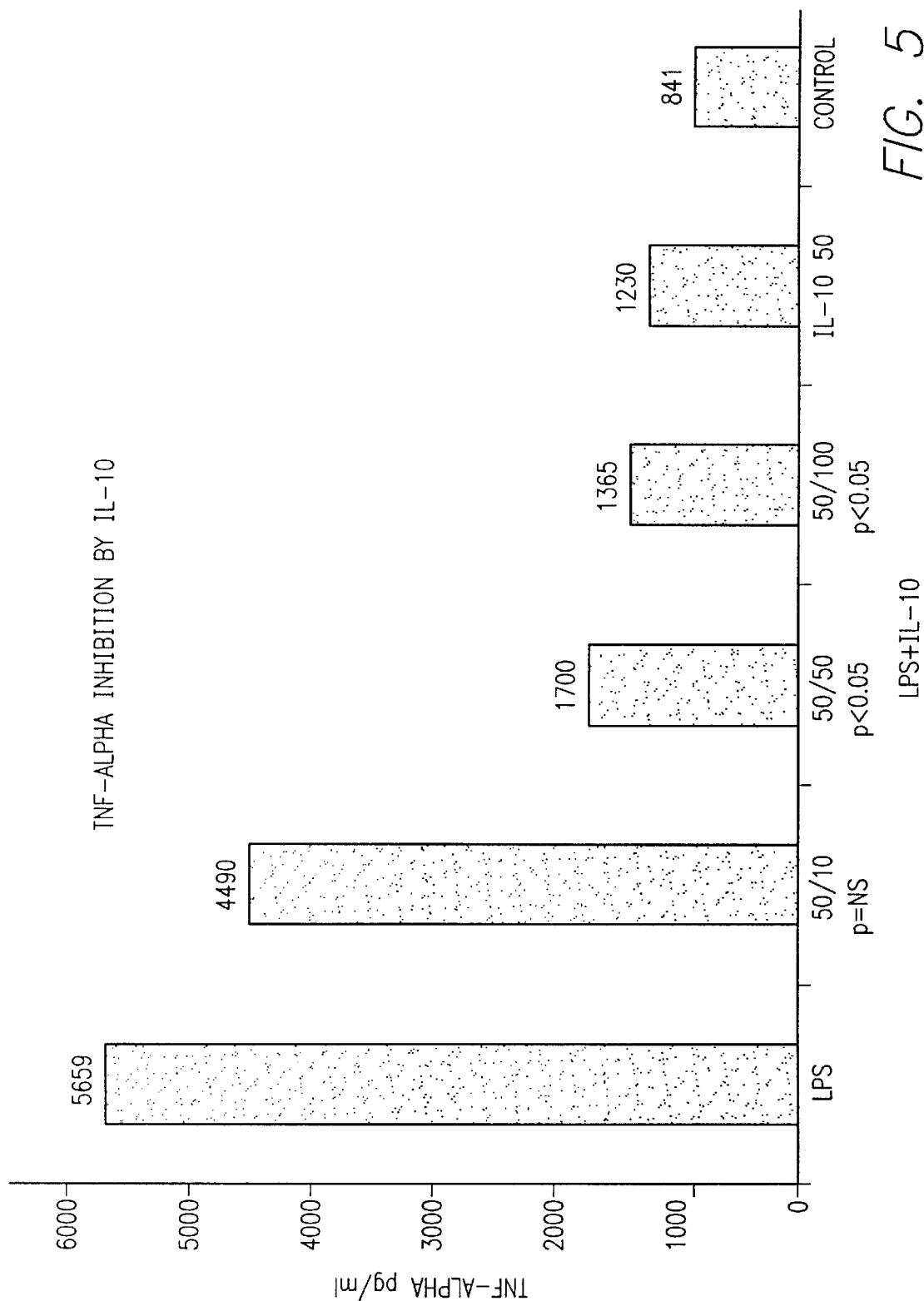

FIG. 5. ELISA results showing a dose-dependent decrease in TNF-α protein secretion from LPS+IL-10 treated tissues.

Figures 6, 7:
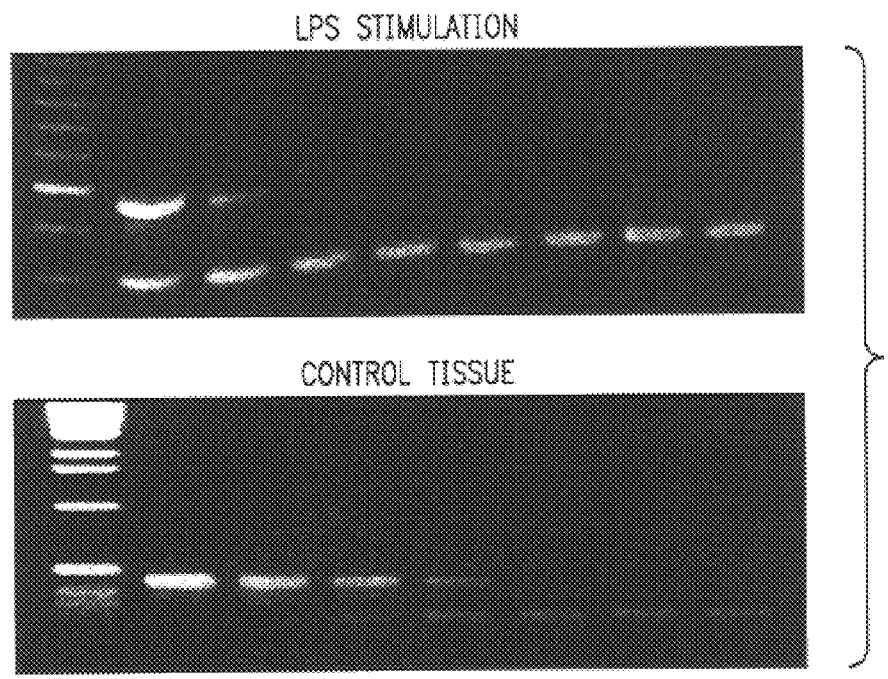

FIG. 6. Bacterial lipopolysaccharide (LPS) stimulates a one hundred-fold increase in IL-8 mRNA expression in cultured amniochorionic membranes, as determined by quantitative PCR. LPS-stimulated tissues produce ~$6 \times 10^6$ IL-6 mRNA transcripts/µl (Lane 1) compared to ~$6 \times 10^3$ transcripts in unstimulated control tissues (Lane 4). Top band represents the MIMIC and bottom band represents the gene specific product.

FIG. 7. Dose-dependent inhibition of IL-8 mRNA expression in lipopolysaccharide (LPS)-stimulated amniochorionic membranes treated with IL-1 0 as determined by PCR. An IL-8 specific band is absent in samples co-stimulated with 50 ng/ml of LPS and 100 ng/ml of IL-10. An IL-8 specific band is visible in samples co-stimulated with 50 ng/ml of LPS and only 50 ng/ml of IL-10. Control and LPS-stimulated tissues show an IL-8 band.

Figure 8:
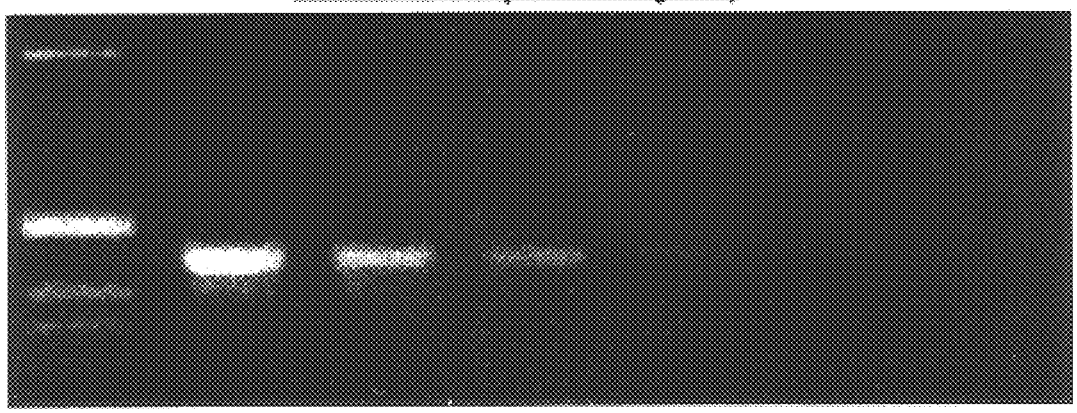
Figure 8:
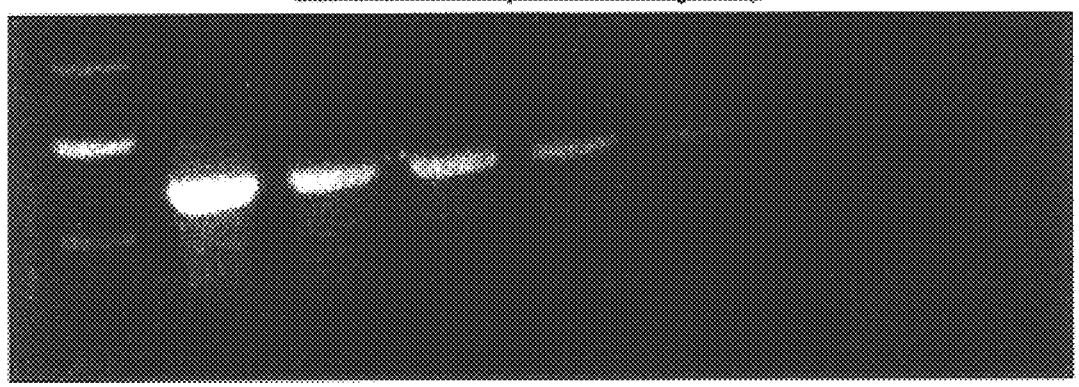

FIG. 8. Dose-dependent inhibition of IL-8 mRNA expression in lipopolysaccharide (LPS)-stimulated amniochorionic membranes treated with IL-10 as determined by quantitative competitive polymerase chain reaction. Top panel: amniochorionic membranes stimulated with 50 ng/ml LPS plus 50 ng/ml IL-10 exhibit a greater than one thousand-fold inhibition of IL-8 mRNA expression (~610 molecules IL-8 mRNA per microliter DNA) compared to membranes treated with LPS alone. In this case a match between the MIMIC and the gene specific bands were seen in lane 5. The IL-8 band was clearly evident in original gels but not clearly reproduced on the photographs. Bottom panel: amniochorionic membranes stimulated with 50 ng/ml LPS plus 100 ng/ml IL-10 exhibit no detectable IL-8 mRNA expression. Only the MIMIC bands were visible in the gels.

Figure 9:
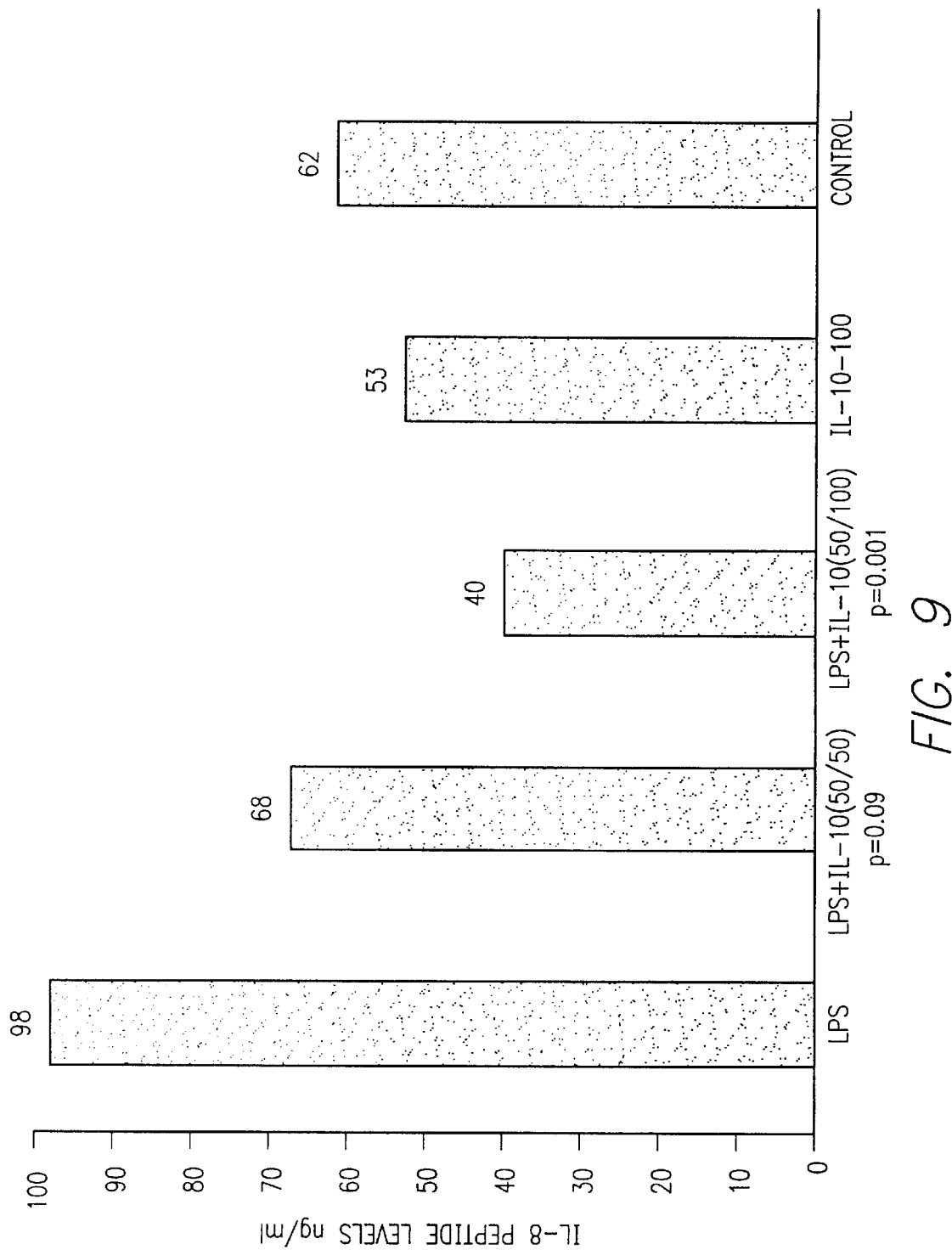

FIG. 9. ELISA results showing a dose-dependent decrease in IL-8 protein secretion from LPS+IL-10 treated tissues. Only at 100 ng/ml of IL-10 was this statistically significant.

Figure 10:
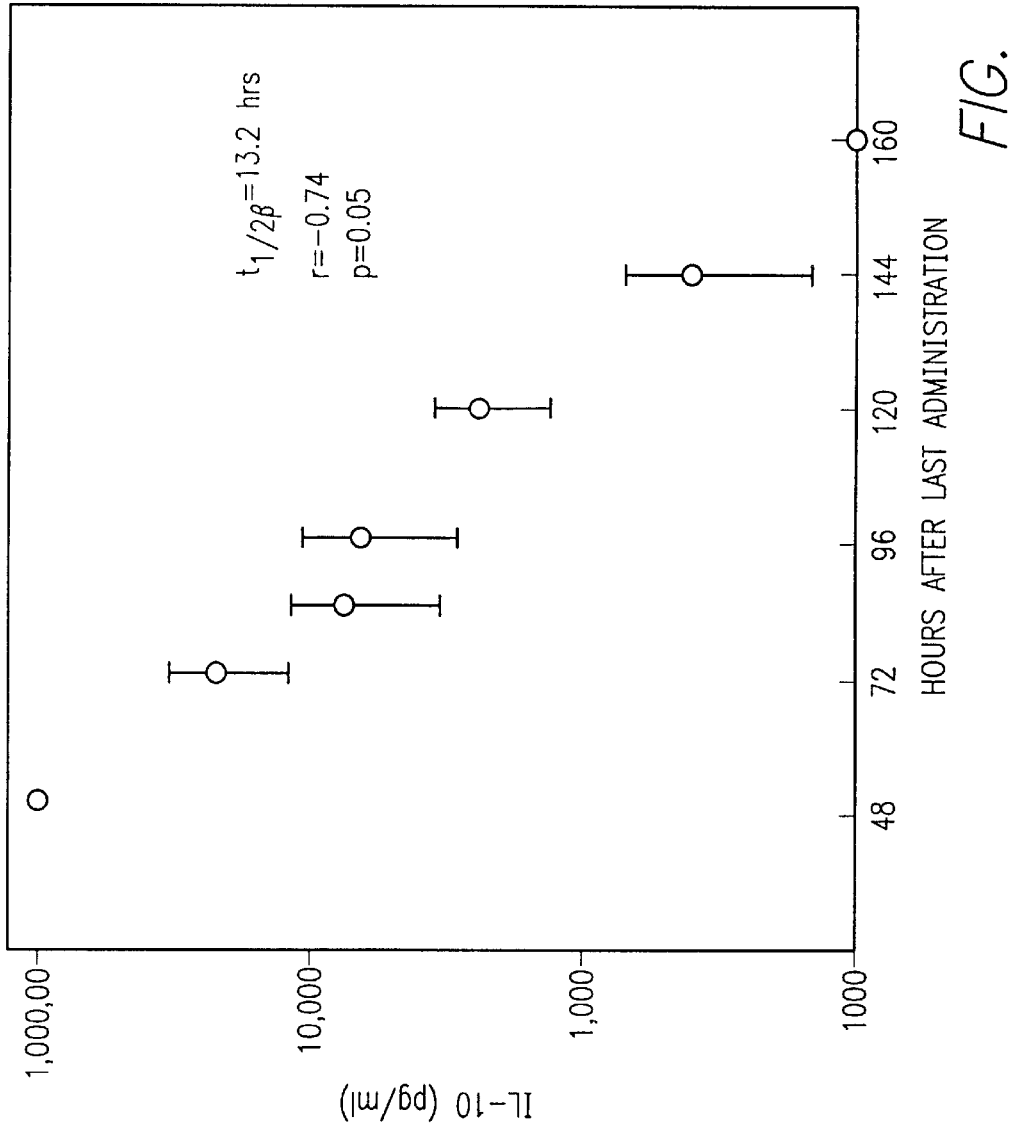

FIG. 10. Elimination half-life of IL-10 within amniotic fluid in rhesus macaques (Example 3, infra).

Figure 11:
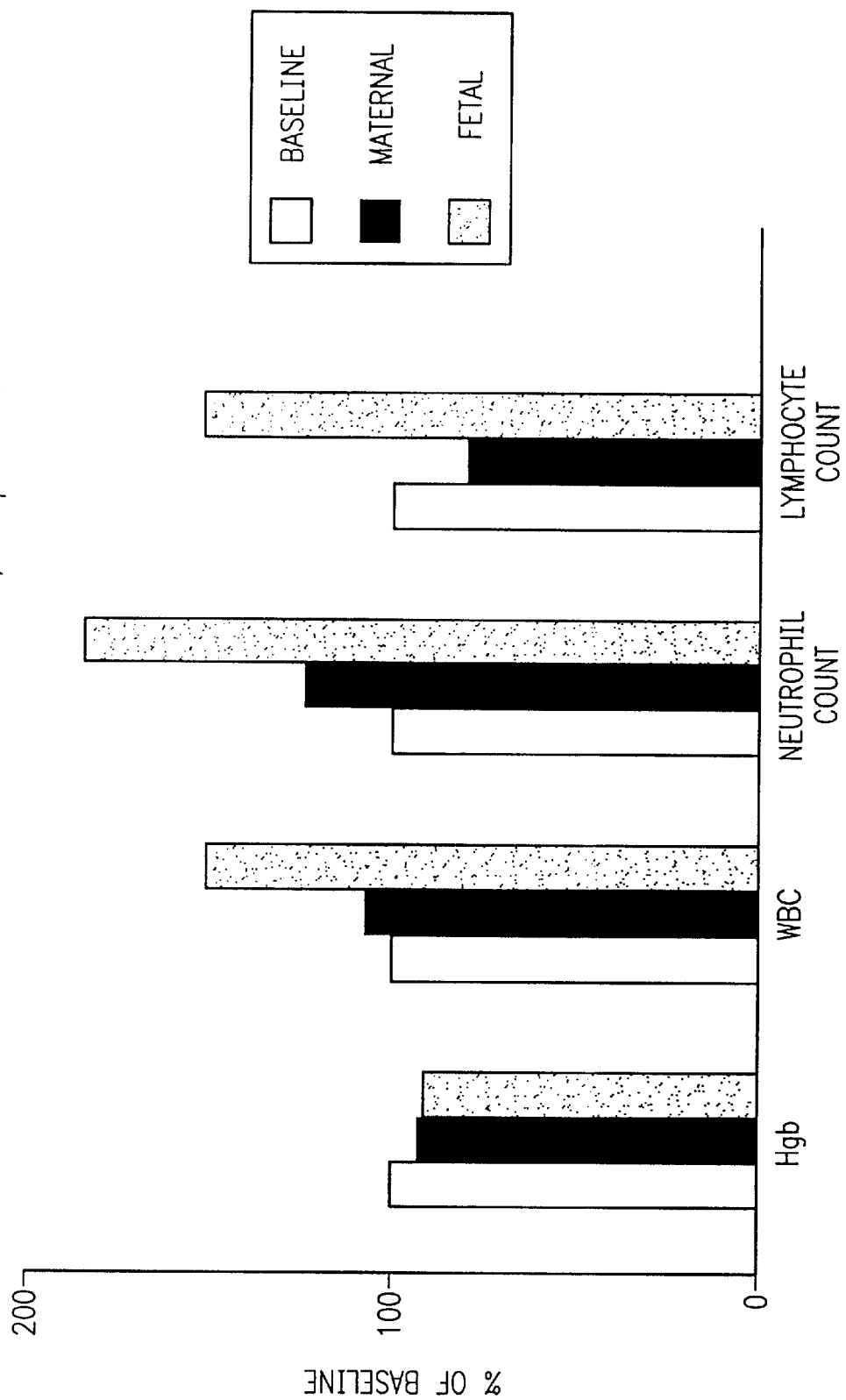

FIG. 11. Effect of IL-10/IL-1µ treatment on maternal and fetal blood pressure and white blood cell, neutrophil and lymphocyte cell counts (Example 3, infra).

DETAILED DESCRIPTION OF THE INVENTION

The present invention provides methods and compositions for preventing and treating preterm labor and premature rupture of fetal membranes. The methods of the invention comprise inhibiting the upregulated expression and/or release of pro-inflammatory cytokines involved in the destructive inflammatory process characteristic of preterm labor and premature rupture of fetal membranes, including those instances of preterm labor and premature rupture associated with microbial invasion of the amniotic cavity and membranes. In one embodiment, the upregulated expression and/or release of the cytokines IL-6, IL-8, and/or TNF-α are inhibited. Preferably, the unregulated expression of each of the cytokines IL-6, IL-8 and TNF-α are inhibited, and more preferably, at the transcriptional level. Any composition capable of inhibiting the upregulated expression of one or more of these cytokines and the resulting inflammatory process in women with intraamniotic infection and/or presenting with preterm labor (regardless of etiology) may be used in the practice of the method of the invention, including but not limited to compositions which directly or indirectly block the transcription, translation and/or secretion of these cytokines from amniochorion, such as, for example, other negative-regulating cytokines or their genes, antisense nucleic acid molecules, or ribozymes capable of inhibiting or blocking the expression of the genes for these cytokines.

The preferred embodiment of the method of the invention involves the use of the cytokine IL-10. As described in detail in the Examples which follow, IL-10 demonstrates the capacity to transcriptionally inhibit the upregulated expression of key inflammatory cytokines involved in the initiation of preterm labor. In vivo studies using IL-10 to prevent experimentally-induced preterm labor in rhesus macaques, also described in the Examples which follow, confirm the utility of this compound in preventing preterm labor.

The methods of the invention are based, in part, upon the conception that the expression of certain inflammatory cytokines which are greatly upregulated in preterm labor form a self-perpetuating cycle of cytokine release that fuels an inflammatory cascade ultimately resulting in preterm labor and premature rupture of the fetal membranes. These cytokines include IL-1, IL-6, 1L-8, and TNF-α. The invention is further based, in part, upon discovering that the cytokine interleukin-10 is capable of transcriptionally inhibiting amniochorionic membrane expression of what applicants believe to be principal inflammatory cytokines involved in promoting an uncontrolled inflammatory cascade that leads to preterm labor, namely IL-6, 1L-8, and TNF-α.

Interleukin-6 is a sensitive and reliable physiologic marker of infection-associated preterm labor. IL-6 is present at very low levels in the amniotic fluid of non laboring women, but is present at higher levels at term and at very high levels during preterm labor. Applicants have established that IL-6 mRNA and protein are present in fetal membranes collected from women with bacterial intraamniotic infection but not in membranes from non-laboring women (Menon et al., 1995, Am J Obstet Gynecol 172: 493–500). Further, IL-6 overexpression can be induced ex vivo by the addition of bacterial endotoxin to cultured membranes (Menon et al., 1995, supra). Applicants have recently shown that IL-10 can inhibit endotoxin-induced overexpression of IL-6 at the transcriptional level (Fortunato et al., 1996, Am J Obstet Gynecol 175: 1057–65).

Interleukin-8 can induce the expression of specific transmembrane glycoproteins by host cells and their specific adhesion molecule counterparts on the surface of polymorphonuclear leukocytes (PMNs) to facilitate PMN binding to the membrane (Fortunato et al., 1995, Am J Reprod Immunol 34:156–162). PMNs migrating to the site of infection can be activated by other locally produced cytokines to release other inflammatory mediators and thereby add to the inflammatory cascade already in progress. Amniochorion Is capable of producing IL-8 and IL-8 production can be induced ex vivo by bacterial toxins. Applicants have observed that IL-8 gene induction leads to constitutive production of IL-8 requiring an inhibitory factor to turn off the gene expression. It is possible that the unique behavior of IL-8 could account for resistant preterm labor in that IL-8 may act as a provocative factor in a self-perpetuating cycle of cytokine release. Even in the face of adequate antimicrobial and tocolytic therapy the continued recruitment and activation of PMNs by IL-8 may itself promote a cycle of cytokine production resulting in resistant preterm labor and delivery.

Tumor necrosis factor-α may play a major role in influencing the outcome of preterm labor-α associated intraamniotic infection. For example, it has been shown that administration of TNF-α to pregnant animals can induce preterm labor and delivery, that TNF-α can induce prostaglandin production from placental tissues, and that TNF-α concentrations are higher in women who have intraamniotic infection and preterm labor than in women without infection (Casey et al., 1989, J Clin Invest 83: 430–436; Romero et al., 1992, Am J Obstet Gynecol 166: 1576–87).

Applicants have previously shown that TNF-α mRNA is a normal product of fetal membranes and that the expression of TNF-α can be induced by bacterial lipopolysaccharide (LPS) (Fortunato et al., 1994, Am J Reprod Immunol 32: 188–195). Although amnion and chorion were shown to produce TNF-α mRNA, the peptide was localized only to amnion cells. Applicants have more recently shown that the amount of TNF-α released from these membranes in response to LPS stimulation was equal to the level of this cytokine seen in the amniotic fluid of women with intraamniotic infection and preterm labor (Fortunato et al., 1996, Am J Obstet Gynecol 174: 1855–62).

In a specific embodiment described herein, interleukin-10 (IL-10) is employed to transcriptionally inhibit upregulated IL-6, IL-8 and TNF-α mRNA expression and inhibit uterine contractility and prevent preterm labor. In another embodiment, IL-10 is used to prevent premature rupture of fetal membranes. In another, related embodiment, a composition which is capable of inducing the expression of IL-10 in situ may be used (an "IL-10 activator"). Such compositions comprise, for example, alpha-melanotropin (α-MSH) or its analogues (e.g., N, O-diacetyl-Ser1-alpha-MSH) (Buckley et al., 1981, Int J Pept Protein Res 17: 508–13; U.S. Pat. No. 5,420,109). In yet another embodiment, the IL-10 gene or other nucleic acid molecules encoding IL-10, preferably under appropriate regulatory control, may be used to transduce cells of the amniochorionic membrane such that the cells express and secrete biologically active IL-10 using techniques well known in the art.

Experimental evidence provided herein establishes that IL-10 can dramatically inhibit the expression of the cytokines IL-6, IL-8 and TNF-α in human amniochorionic membranes at the transcriptional level. More specifically, applicants have determined that IL-10 inhibits the upregulation of IL-6, IL-8, and TNF-α expression induced in amniochorionic membranes stimulated with bacterial lipopolysaccharide, a process which applicants have determined mimics the challenge that microbial infection presents to the amniochorion in vivo. As described more fully in the examples which follow, treatment of amniochorionic membranes ex vivo with IL-10 results in a 100-fold inhibition of endotoxin-mediated overexpression of TNF-α mRNA and secreted protein at an IL-10 dose of 100 ng/ml. In addition, IL-10 completely inhibits endotoxin-mediated overexpression of IL6 in amniochorionic membranes at the same dose. Similarly, IL-10 virtually eliminates endotoxin-mediated overexpression and secretion of IL-8 at this dose. Interestingly, as shown by the data generated in Examples 1 and 2, below, the presence of a stimulatory agent and activation of the IL-8 and TNF-α genes above control values is required for IL-10 inhibition of these cytokines in amniochorionic membrane. A similar action by IL-10 on fetal membrane production of IL-6 has been observed (Fortunato et al., 1996, Am J Obstet Gynecol 175:1057–65).

Accordingly, the invention provides methods of treating preterm labor and preventing premature rupture of the fetal membranes by inhibiting the elevated expression of IL-6, IL-8, and/or TNF-α in amniochorionic membranes exposed to microbial infection, which comprises contacting the amniochorionic membrane with an amount of IL-10 sufficient for transcriptionally inhibiting such elevated expression. Preferably, IL-10 is used at a concentration sufficient for inhibiting the overexpression of each of IL-6, IL-8, and TNF-α. A related method comprises contacting the amniochorionic membrane with an amount of IL-10 activator sufficient to result in the expression of IL-10 at levels sufficient for transcriptionally inhibiting the elevated expression of IL-6, IL-8, and/or TNF-α (preferably all).

The invention further provides a method of preventing and treating preterm labor, which method comprises administering IL-10 or an IL-10 activator to a pregnant mammal presenting symptoms of preterm labor and/or premature rupture of fetal membranes, at a dose sufficient to inhibit uterine contractility and labor progression. The invention also provides a method of preventing premature rupture of the fetal membranes, which method comprises administering IL-10 to a pregnant mammal presenting symptoms of preterm labor and/or premature rupture of the fetal membranes at a dose sufficient to inhibit premature rupture of the fetal membranes. Symptoms of preterm labor include premature uterine contractions (i.e., before week 36 gestation in humans), positive fibronectin, and cervical effacement and dilatation.

The invention further provides a method of preventing and treating preterm labor or premature rupture of the fetal membranes associated with intraamniotic infection, which comprises administering IL-10 or an IL-10 activator to a pregnant mammal presenting with symptoms of an intraamniotic infection, at a dose sufficient to inhibit the expression of at least one of the cytokines IL-6, IL-8, and TNF-α in the amniochorion and/or prevent uterine contractility and premature labor or premature rupture of the fetal membranes. In one embodiment, the IL-10 activator is administered at a dose sufficient to inhibit the overexpression of each of IL-6, IL-8 and TNF-α.

As used herein, "IL-10" means human interleukin-10 protein as well as allelic variants, conservative substitution mutants, or mammalian homologues which retain IL-10 biological activity. As used herein, "IL-10 biological activity" means the ability to inhibit the expression of one or more inflammatory cytokines produced by amniochorion in response to microbial infection of the amniochorion, and/or the ability to inhibit or diminish the inflammatory response in amniochorion induced by intraamniotic infection, and/or the ability to prevent premature rupture of the amniochorionic membrane in women with intraamniotic infection. The extent to which (and the dose at which) a particular IL-10 is effective at preventing premature rupture and preterm labor may be tested and evaluated using the ex vivo amniochorionic membrane culture system described in the Examples presented herein or in vivo using suitable animal models. For the treatment of women with intraamniotic infection, a human IL-10 is preferred, such as human recombinant IL-10 which is widely available form commercial sources. Recombinant human IL-10 administered as single doses by intravenous injection is well tolerated in human subjects, and the pharmacokinetics and pharmacodynamics of recombinant human IL-10 have been studied (see, for example, Huhn et al., 1997, Clin Pharmacol Therap 62:171–180 and the publications cited therein).

In the practice of the method of the invention, any route of administration of an IL-10 or an IL-10 activator which results in the inhibition of microbially-induced overexpression of IL-6, IL-8, TNF-α, and/or other cytokines involved in the inflammatory process associated with intraamniotic infection may be employed, including but not limited to intraamniotic, intrauteral, intravenous, subcutaneous, and intramuscular administration.

The dose of IL-10 or IL-10 activator used in the practice of the method of the invention will depend on various factors, including but not limited to the nature and extent of infection, the route of administration, as well as various clinical considerations. Doses for intravenous administration may be in the range of 25 to 50 $\mu$g/kg or higher. Dosages for intraamniotic administration may be significantly lower due to decreased volume of distribution.

In a preferred embodiment, IL-10 is initially administered intraamniotically and intravenously as infusions in appropriately preserved solutions of, for example, phosphate buffered saline (PBS) or another appropriate buffer, at doses of between approximately 1 and 10 mg. Treatment will generally involve the multiple administrations of the IL-10 preparation. It may be preferable for the initial dose to be administered as an intraamniotic infusion with or without intravenous co-α administration. Subsequent doses are preferably administered intravenously, although intraamniotic infusions may also be acceptable depending upon the patient'response to the initial dose. However, as one of skill in the art will understand, various factors will influence the ideal dose regimen.

Preterm labor and premature rupture of the fetal membranes may be treated with IL-10 alone or in combination with other agents, including for example, tocolytic agents and antibiotics.

The invention also provides a pharmaceutical composition comprising IL-10 and, optionally, a suitable pharmaceutical carrier, for use in the treatment of intraamniotic infection and associated preterm labor. The invention additionally provides a pharmaceutical composition comprising an IL-10 activator and, optionally, a suitable pharmaceutical carrier, for use in the treatment of intraamniotic infection and associated preterm labor. Suitable carriers for pharmaceutical compositions include any material which when combined with the IL-10 or IL-10 activator retains the molecule'activity and is non-reactive with the subject's immune system. Examples include, but are not limited to, various standard pharmaceutical carriers such as phosphate buffered saline solution, water, emulsions such as oil/water emulsion, and various types of wetting agents. Other carriers may also include sterile solutions, tablets, etc. Typically, such carriers contain excipients such as starch, milk, sugar, certain types of clay, gelatin, stearic acid or salts thereof, magnesium or calcium stearate, talc, vegetable fats or oils, gums, glycols, or other known excipients. Excipients which have utilized in the administration of IL-10 in other indications include sodium citrate dihydrate, sucrose, and glycine mixtures. Compositions comprising such carriers are formulated by well known conventional methods.

EXAMPLES

The invention is further described and illustrated by way of the following examples and the experimental details therein. This section is set forth as an aid to understanding the invention, but is not intended to, nor should it be construed as, limiting the scope of the invention.

Example 1

Interleukin-10-Mediated Inhibition of TNF-α mRNA and Protein Expression in Amniochorionic Membranes Ex Vivo Materials and Methods Ex Vivo Organ Culture of Amniochorionic Membranes Placentas (n=4) were obtained from uncomplicated gestations at term undergoing elective repeat cesarean section (C-section) prior to the onset of labor. Membranes were harvested under strictly sterile conditions. Amniochorionic membranes were dissected free of the placenta and were placed in PBS with heparin 100 U/ml, penicillin 100 U/ml, streptomycin 100 mg/ml, and amphotericin B 0.25 mg/ml. All adherent blood clots were removed using sterile cotton gauze. Portions of cleared membrane without decidual contamination, adherent clots, or blood vessels were cultured in an organ explant system as previously described (Fortunato et al., 1994, Am J Reprod Immunol 32: 188–195). Briefly, membranes were washed in HBSS with antibiotics, and pieces of tissue were cut into circles using a 6 mm skin biopsy punch (Euro-Med Cooper Surgical, Richmond, Va.). Tissues were then washed in 3 changes of HBSS supplemented with antibiotics. The membrane discs were placed in Falcon 9 mm cell culture inserts which were then placed in a Falcon 24 well tissue culture plate. The culture medium consisted of Dulbecco's modified Eagle's medium with Ham's F12 nutrient mixture (1:1), antibiotics as above, 2 mM glutamine, and 15% heat inactivated fetal bovine serum (all from Sigma, St. Louis Mo.). Media and fetal bovine serum used in this culture system contained the lowest endotoxin levels commercially available (<0.05 ng/ml). The cell culture insert contained 0.2 ml and the culture well 0.6 ml of medium. Cultures were incubated at 37 ° C. in an atmosphere of 5%$CO_2$:room air and media were changed on a daily basis.

Bacterial Lipopolysaccharide and IL-10 Treatments

Amniochorion tissues were incubated for a period of 48 hrs before stimulation. This was done to achieve a base line expression of cytokines as defined in earlier studies (Menon et al., 1995, Am J Obstet Gynecol 172: 493–500). LPS, (E.coli 055:B5, Sigma chemicals, St. Louis, Mo.) and recombinant IL-10 (R&D Systems, Minneapolis, Minn.) were added to the culture medium as described herein. Cultures were stimulated with either LPS (50 ng/ml); LPS and IL-10 (50/50 ng/ml and 50/100 ng/ml); or IL-10 alone (100 ng/ml). Tissues were harvested at the end of a 24 hr stimulation and frozen in liquid $N_2$ for RNA extraction and analysis. Media were collected and stored at —20 ° C. for enzyme linked immunosorbent assay (ELISA). Media blanks with the appropriate dilutions of LPS and IL-10 were incubated without tissue for use as ELISA controls.

RT-PCR Assay for TNF-α mRNA Expression

RNA was extracted using TRIzol reagent (GIBCO-BRL, Gaithersburg, Md.) according to the manufacturers instructions. 1 ml of reagent was used for two pieces of tissues (6 mm). For basic RT-PCR, 0.5 mg of total RNA was subjected to random primed (GIBCO-BRL) cDNA synthesis followed by 30 cycles of PCR in a Perkin-Elmer thermocycler (Perkin-Elmer Cetus, Norwalk, Conn.) using specific primers for TNF-α (Fortunato et al., 1994, Am J Reprod Immunol 32: 188–195). The products were analyzed on an ethidium bromide stained 1.5% agarose gel. The expected fragment length for the TNF-α band was 124 bp. GAPDH, a housekeeping gene, was used as an internal control and its fragment size was expected to be 248 bp.

Semi-quantitative Determination of TNF-α mRNA by Quantitative Competitive Polymerase Chain Reaction Quantitative Competitive PCR (QPCR) was performed using the human tumor necrosis factor-α PCR MIMIC and human TNF-α amplifier set (CLONTECH, Palo Alto, Calif.). In this competitive PCR assay one set of primers is used to amplify both the target gene cDNA and another neutral DNA fragment (MIMIC DNA). The neutral DNA fragment competes with the target cDNA fragment for the same primers (TNF-α mRNA specific) and acts as an internal standard by providing a PCR product of different size. This protocol used a non-homologous DNA fragment engineered to contain the desired gene template primers and thus was recognized by a pair of gene specific primers. Serial dilutions of the PCR MIMICs were added to PCR amplification reactions containing constant amounts of experimental cDNA samples. A constant amount of the CDNA was then co-amplified with known concentrations of the competitor DNA for 30 cycles (the concentration of MIMIC used ranged between $6 \times 10^6$ and 60 molecules per ml). This MIMIC utilizes the same primer as the target CDNA but yields a PCR product of different size. Following PCR, the products were resolved by 1.6% agarose gel electrophoresis and visualized on an ethidium bromide stained gel. A visual comparison was made of the intensities of the bands produced by the target gene and the PCR MIMIC. When the intensity of target gene product band equals that of the PCR MIMIC band, the molar concentrations of both are equal. Since the molar concentrations of the MIMIC were known, the relative levels of expression of target mRNA could be estimated (numberfold increase/decrease). The expected fragment lengths of the MIMIC and gene specific bands were 617 bp and 444 bp respectively.

Enzyme Linked Immunosorbent Assay for TNF-α

The release of TNF-α into the culture medium was quantitated using ELISA. The assay procedure involved a multiple-site two step sandwich immunoassay using monoclonal antibody (Medgenix, IncStar Corporation, Stillwater, Minn.). Manufacturers instructions were followed to perform ELISA. Briefly, the culture media were diluted in plain media and standard curves were developed using duplicate samples of known quantities of recombinant human TNF-α. Media concentrations were determined by relating the absorbance obtained to the standard curve by linear regression analysis. Controls consisted of plain media and LPS and IL-10 containing media incubated in wells without tissue. Controls and internal standards contained in the kits was also included in the assay procedure. Colorimetric absorption was read at 450 and 650 nm using an Inc Star Automatic microplate reader.

RESULTS

Amniochorion showed expression of TNF-α mRNA both from cultured and uncultured membrane. The initial manipulation of placing the tissue in culture was accompanied by an increase in both mRNA expression and peptide production which fell to baseline levels by 48 hrs in culture. After 48 hrs, LPS was capable of stimulating TNF-α expression (Fortunato et al., 1994, Am J Reprod Imunol 32:188–95). No TNF-α expression was seen after 4 days in culture, even when tissues were stimulated with LPS. ELISA results documented increased levels of TNF-α peptide release from LPS stimulated tissues when compared with control experiments (FIG. 1).

Quantitative competitive PCR was performed to confirm the changes in TNF-α mRNA expression. Amniochorionic membranes stimulated with 50 ng/ml of LPS produced approximately (~) 60,000 molecules of TNF-α mRNA/µl of DNA (FIG. 2), whereas control samples from the same experiment produced no TNF-α mRNA. When membranes were simultaneously stimulated with LPS and IL-10 (50 and 100 ng/ml), a dose dependent decrease in the production of TNF-α mRNA was noticed. Tissues stimulated with LPS+ IL–10 (50/50 ng/ml) produced ~6,000 molecules of TNF-α mRNA and only - 600 molecules/µl of DNA were seen when the dose of IL-10 was increased to 100 ng/ml along with 50 ng/ml of LPS (FIGS. 3A and B).

The effect of IL-10 treatment was then tested in vitro mimicking pre and post infectious condition. For this, after a 48 hr incubation, amniochorionic membranes were stimulated with LPS (50 ng/ml) or IL-10 (100 ng/ml) for a period of 6 hrs. Media were then replaced with IL-10 containing media in LPS treated tissues and with LPS media in IL-10 treated tissues and incubated for another 18 hrs. Basic PCR results demonstrated expression of TNF-α mRNA from each of these samples, whereas controls remained negative as expected after 72 hrs incubation (FIG. 4). When LPS stimulation was performed in the presence of IL-10 (50/100) maximum inhibition was seen and this was confirmed by QPCR as shown in FIG. 3.

The inhibition of TNF-α mRNA by IL-10 was then confirmed at the protein level by performing ELISA on media samples collected from these experiments. A dose dependent decrease in TNF-α levels was observed in samples treated simultaneously with LPS and IL-10. In tissues treated with IL-10 alone, levels of TNF-α remained close to that of control levels. (FIG. 5).

Example 2

Interleukin-10-MEDIATED Inhibition of IL-8 mRNA and Protein Expression in Amniochorionic Membranes Ex vivo

MATERIALS AND METHODS

Ex Vivo Organ Culture of Amniochorionic Membranes

Was conducted as described in Example 1, above.

Bacterial Lipopolysaccharide and IL-10 Treatments

Amniochorion tissues were incubated for a period of 48 hrs before stimulation. This was done to achieve a base line expression of cytokines as defined in earlier studies (Menon et al., 1995, Am J Obstet Gynecol 172: 493–500). LPS, (E.coli 055:B5, Sigma chemicals, St. Louis, Mo.) and recombinant IL-10 (R&D Systems, Minneapolis, Minn.) were added to the culture medium as described herein. Cultures were stimulated with either LPS (50 ng/ml); LPS and IL-10 (50/50 ng/ml and 50/100 ng/ml); or IL-10 alone (100 ng/ml). Tissues were harvested at the end of a 24 hr stimulation and frozen in liquid $N_2$ for RNA extraction and analysis. Media were collected and stored at −20° C. for enzyme linked immunosorbent assay (ELISA). Media blanks with the appropriate dilutions of LPS and IL-10 were incubated without tissue for use as ELISA controls.

RT-PCR Assay for IL-8 mRNA Expression

RNA was extracted using TRIzol reagent (GIBCO-BRL, Gaithersburg, Md.) according to the manufacturers instructions. 1 ml of reagent was used for two pieces of tissues (6 mm). For basic RT-PCR 0.5 mg of total RNA was subjected to random primed (GIBCO-BRL) cDNA synthesis followed by 30 cycles of PCR in a Perkin-Elmer thermocycler (Perkin-Elmer Cetus, Norwalk, Conn.) using primers specific for IL-8 (Fortunato et al., 1995, Am J Reprod Immunol 34:156–162). The products were analyzed on an ethidium bromide stained 1.5% agarose gel. The expected fragment length for the IL-8 band was 302 bp. GAPDH, a house keeping gene, was used as an internal control and its fragment size was expected to be 248 bp.

Quantitative PCR Assay for IL-8 mRNA Expression

QPCR was performed using the quantitative PCR construction kit (CLONTECH, Palo Alto, Calif.). In this competitive PCR assay one set of primers is used to amplify both the target gene cDNA and another neutral DNA fragment (MIMIC DNA) (Fortunato et al., 1994, Am J Reprod Immunol 32: 188–193). The neutral DNA fragment competes with the target cDNA fragment for the same primers (IL-8 mRNA specific) and acts as an internal standard by providing a PCR product of different size. This protocol used a non-homologous DNA fragment engineered to contain the desired gene template primers and thus was recognized by a pair of gene specific primers. Serial dilutions of the PCR MIMICs were added to PCR amplification reactions containing constant amounts of experimental cDNA samples. A constant amount of the cDNA was then co-amplified with known concentrations of the competitor DNA for 30 cycles (the concentration of MIMIC used ranged between $6 \times 10^6$ and 60 molecules/ml). This MIMIC utilizes the same primer as the target cDNA but yields a PCR product of different size. Following PCR, the products were resolved by 1.5% agarose gel electrophoresis and visualized on an ethidium bromide stained gel. When the intensity of the target gene product band equals that of the PCR MIMIC band, the molar concentrations of both are equal. Quantitation was achieved by gel band spot densitometry using the Alpha Ease software program (Alpha Innotech Corporation, San Leandro, Calif.). Integrated density values for two matching bands (MIMIC and IL-8) were obtained and the densitometric ratio was calculated. This value was multiplied by the known concentration of the MIMIC to determine the approximate (~) number of molecules. Since the molar concentrations of the MIMIC were known, the relative levels of expression of target mRNA could be estimated (numberfold increase/decrease). The expected fragment lengths of the MIMIC and gene specific bands were 449 bp and 303 bp respectively.

Enzyme Linked Immunosorbent Assay for IL-8

The release of IL-8 into the culture medium was quantitated using ELISA. The assay procedure involved a multiple-site two step sandwich immunoassay using monoclonal antibody (Medgenix, IncStar Corporation, Stillwater, Minn.). Manufacturers instructions were followed to perform ELISA. Briefly, the culture media were diluted in plain media and standard curves were developed using duplicate samples of known quantities of recombinant human IL-8. Media concentrations were determined by relating the absorbance obtained to the standard curve by linear regression analysis. Controls consisted of plain media and LPS and IL-10 containing media incubated in wells without tissue. Controls and internal standards contained in the kits were also included in the assay procedure. Colorimetric absorption was read at 450 and 650 nm using an Inc Star Automatic microplate reader. Parametric and non parametric statistics were used to compare continuous data as appropriate. A p value of <0.05 was considered significant.

Results

When cultured fetal membranes were stimulated with LPS a 100 fold increase in the expression of IL-8 mRNA was observed. QPCR results showed production of ~$6.6 \times 10^6$ molecules of IL-8 mRNA/$\mu$l from tissues stimulated with bacterial LPS, whereas control tissues showed only 6380 molecules/$\mu$l (FIG. 6).

The inhibitory effects of IL-10 during an infectious process in vivo were reproduced by stimulating the membrane with different doses of IL-10 in the presence of a fixed concentration of LPS. Basic PCR demonstrated a total inhibition of IL-8 mRNA in membranes stimulated with LPS+IL-10 (50/100 ng/ml) (FIG. 7), whereas amplifiable amounts of mRNA were seen in tissues treated with LPS+IL-10 (50/50 ng/ml). These results were confirmed by performing QPCR on the same samples of mRNA. In membranes simultaneously stimulated with LPS and IL-10 (50/50 and 50/100 ng/ml), a dose dependent decrease and inhibition of IL-8 expression was observed. Tissues treated with LPS+IL-10 (50/50) produced ~610 molecules of IL-8 mRNA/$\mu$l (See lane 5; FIG. 8), whereas no amplifiable IL-8 molecules were seen in tissues when the dose of IL-10 was increased to 100 ng/ml (FIG. 8) (compared to ~$6.6 \times 106$ molecules/$\mu$l when stimulation was performed with LPS alone; FIG. 6). This result supported our basic RT-PCR data. Tissues were then stimulated with IL-10 alone in the absence of LPS. No visible change in basic RT-PCR or QPCR band intensities were seen when compared with control.

The effect of IL-10 on IL-8 mRNA expression was then confirmed at the protein level by performing ELISA on media samples collected from these experiments. A dose-dependent decrease in IL-8 release was seen from tissues simultaneously stimulated with LPS and IL-10 (FIG. 9). Treatment with IL-10 alone did not seem to have an effect on IL-8 production and levels from these media samples remained similar to control levels.

Example 3

IL-10 Mediated Inhhibtion of Uterine Contractility in Rhesus Monkeys

MATERIALS AND METHODS:

Four chronically instrumented pregnant rhesus macaques were treated with intravenous (25 $\mu$g/kg, 3 times daily) and intraamniotic (100 $\mu$g/kg, 3 times daily) infusions of recombinant IL-10 for three days. After the first dose, all animals received intraamniotic infusions of 10 $\mu$g of IL-1$\beta$ in order to stimulate uterine contractility and labor. In addition, each animal received further intraamniotic infusions of IL-1$\beta$, alone, at 7 and 14 days after treatment with IL-10 and IL-1$\beta$. In order to evaluate dose parameters, the elimination half-life of IL-10 within amniotic fluid was determined.

Uterine contractility (HCA; hourly contraction area), and amniotic fluid (AF) concentrations of IL-1$\beta$, IL-10, TNF, and prostaglandins $E_2$ ($PGE_2$) and $F_{2a}$ ($PGF_{2a}$) were serially determined before, during and after each infusion. A standard uterine contractility index used in primate research was adopted, wherein labor is judged to be present at 10,000 mm Hg sec/hr.

In order to evaluate the safety of the treatment protocol, white blood cell, neutrophil and lymphocte counts were monitored for potential IL-0.10-induced immune response inhibition. Maternal and fetal blood pressure and arterial blood gases were also monitored.

Results

Treatment of pregnant rhesus macaques with IL-10 resulted in an essentially complete inhibition of 10$\mu$g of IL-1$\beta$-induced preterm uterine contractility on the first day of treatment. This effect remained 7 days after IL-10 treatment. No inhibition of the immune response or any effect on either maternal or fetal blood pressure or arterial blood gas concentrations were observed.

Specifically, as shown in TABLE 1 below, treatment with IL-10 significantly reduced I1β induced contractility when administered concurrently with IL-1β, by approximately 85% (*p<0.05), when compared to IL-1β infusion alone 14 days later, when AF IL-10 was no longer detected. Uterine contractility in the treated animals was inhibited to 2,375 mm Hg sec/hr on day 1, and to 2,810 mm Hg sec/hr on day 7, as compared to a level of 15,870 mm Hg sec/hr at day 14 when IL-10 concentrations had fallen to zero. Labor is generally regarded as present at a level of 10,000 mm Hg sec/hr or greater in this animal model. Thus, the infusions of IL-10 were capable of inhibiting the onset of labor for a prolonged period. Effects on maternal and fetal blood gases were not observed (TABLE 1).

Between 0 and 14 days, an inverse relationship between AF IL-10 concentration and uterine contractility was noted. Therapeutic concentrations of IL-10 remained for at least 7 days, as strong inhibition was observed at day 7 when IL-10 concentrations had dropped to 4 ng/ml (compare with day 1 levels IL-10 of over 100 ng/ml). The half-life of IL-10 within the amniotic fluid was measured at 13.2 hours (FIG. 10).

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method of treating preterm labor, comprising administering IL-10 to a pregnant human presenting (a) symptoms of preterm labor accompanied by elevated levels of IL-6, IL-8 and TNF-α in the amniotic fluid, or (b) symptoms of preterm labor and intraamniotic microbial infection, at a dose sufficient to inhibit intrauterine contractility and labor progression.

2. The method of claim 1, wherein the IL-10 is administered intraamniotically.

3. The method of claim 1, wherein the IL-10 is administered intravenously.

4. A method of treating preterm labor, comprising administering the IL-10 activator a-MSH or an a-MSH analog to a pregnant human presenting (a) symptoms of preterm labor accompanied by elevated levels of IL-6, IL-8 and TNF-α in the amniotic fluid, or (b) symptoms of preterm labor and intraamniotic microbial infection, at a dose sufficient to inhibit intrauterine contractility and labor progression.

5. The method of claim 4, wherein the IL-10 activator is administered intraamniotically.

6. The method of claim 4, wherein the IL-10 activator is administered intravenously.

7. A method of treating preterm labor, comprising inhibiting the expression of IL-6, IL-8, and TNF-α in the amnio-

TABLE 1

EFFECT OF IL-10/IL-1β TREATMENT

|  | BASELINE | IL-10 + IL-1β DAY 1 | IL-1β DAY 7 | IL-1β DAY 14 |
|---|---|---|---|---|
| UTERINE CONTRACTILITY (HCA; mm Hg sec/hr) | 1,000 | 2,375 | 2,810 | 15,870 |
| CYTOKINE CONCENTRATION (ng/ml) | | | | |
| IL-1β | 0 | 34.79 | 21.5 | 21.0 |
| IL-10 | 0 | 104.1 | 4.0 | 0 |
| TNF | 0.08 | 0.36 | 0.31 | 0.84* |
| IL-1ra | 5.71 | 43.35* | 33.25* | 52.9* |
| PROSTAGLANDIN CONCENTRATION (ng/ml) | | | | |
| PGE2 | 0.28 | 6.36* | 10.7* | 8.0* |
| PGF2a | 0.14 | 0.74* | 0.66* | 1.13* |
| Maternal Arterial Blood Gases | | | | |
| pH | 7.48 +/− 0.01 | 7.48 +/− 0.01 | | |
| pO2 | 110.3 +/− 3.4 | 105.4 +/− 2.9 | | |
| Fetal Arterial Blood Gases | | | | |
| pH | 7.48 +/− 0.01 | 7.48 +/− 0.01 | | |
| pO2 | 35.3 +/− 0.9 | 36.2 +/− 1.9 | | |

*p 0.05 compared to baseline
IL-1ra = IL-1 receptor antagonist

Treatment with IL-10 had no effect on blood pressure or arterial blood gases, either for mother or fetus. No significant inhibition of maternal or fetal white or immune cells was observed (FIG. 11). In fact, slight increases in maternal white blood cell and neutrophil counts, and significant increases in fetal white blood cell, neutrophil and lymphocyte counts, were observed in the study. No other adverse reactions were noted. These data suggest that the IL-10 treatment of infection-induced preterm labor is both safe and effective.

chorionic membranes of a pregnant human presenting (a) symptoms of preterm labor accompanied by elevated levels of IL-6, IL-8 and TNF-α in the amniotic fluid, or (b) symptoms of preterm labor and intraamniotic microbial infection, wherein the inhibition of the expression of IL-6, IL-8, and TNF-α is achieved by contacting the amniochorionic membrane with IL-10 at a dose sufficient to transcriptionally inhibit such expression.

\* \* \* \* \*